(12) United States Patent
Ratts et al.

(10) Patent No.: US 10,989,654 B2
(45) Date of Patent: Apr. 27, 2021

(54) OPTICAL SENSOR FOR AFTERTREATMENT CATALYST CONDITION

(71) Applicant: Caterpillar Inc., Deerfield, IL (US)

(72) Inventors: Joshua L. Ratts, East Peoria, IL (US); Wilce Damion Williams, San Antonio, TX (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 16/377,381

(22) Filed: Apr. 8, 2019

(65) Prior Publication Data

US 2020/0319094 A1  Oct. 8, 2020

(51) Int. Cl.
*G01N 21/3504* (2014.01)
*G01N 33/00* (2006.01)

(52) U.S. Cl.
CPC ..... *G01N 21/3504* (2013.01); *G01N 33/0036* (2013.01)

(58) Field of Classification Search
CPC .......... G01N 21/3504; G01N 33/0036; G01N 21/359; G01N 33/0047; G01N 2021/1795; G01N 2021/3513; G01N 21/33; G01N 21/3518; G01N 21/39; G01N 2201/06113; G01N 33/0062; G01N 5/02; B60W 50/14; F01N 13/008; F01N 2430/00; F01N 2560/023; F01N 2560/06; F01N 2560/07; F01N 2570/12; F01N 2900/0418; F01N 2900/0601; F01N 2900/08; F01N 2900/1402; F01N 2900/1404; F01N 2900/1411; F01N 3/021; F01N 3/0835; F01N 3/103; F01N 3/2066; F01N 9/00; F01N 9/005; F02D 2200/08; F02D 41/027; F02D 41/1459; Y02T 10/24; Y02T 10/47

See application file for complete search history.

(56) References Cited

U.S. PATENT DOCUMENTS

| | | | | |
|---|---|---|---|---|
| 4,668,635 A | * | 5/1987 | Forster ................. | G01N 33/004 436/134 |
| 5,060,505 A | * | 10/1991 | Tury .................... | G01N 21/274 250/339.09 |
| 5,077,970 A | * | 1/1992 | Hamburg .............. | F01N 11/007 60/274 |
| 5,099,680 A | * | 3/1992 | Fournier ............. | G01M 15/102 73/114.71 |
| 5,475,223 A | * | 12/1995 | Carter, III .......... | F02D 41/1451 250/339.06 |
| 5,964,089 A | * | 10/1999 | Murphy ................. | F01N 11/00 60/286 |

(Continued)

*Primary Examiner* — Mohamed K Amara
(74) *Attorney, Agent, or Firm* — Hibshman Claim Construction PLLC

(57) ABSTRACT

An aftertreatment system for an engine system is disclosed. The aftertreatment system may comprise an optical sensor mounted on the aftertreatment catalyst. The optical sensor may include a light source configured to illuminate the aftertreatment catalyst with light and a detector configured to measure an amount of the light absorbed by the aftertreatment catalyst upon illumination with the light. The measured amount of the light absorbed by the aftertreament catalyst may correlate with a condition parameter (e.g., hydrocarbon loading, oxidation state, etc.) of the aftertreatment catalyst.

17 Claims, 6 Drawing Sheets

(56) References Cited

U.S. PATENT DOCUMENTS

| | | | |
|---|---|---|---|
| 5,996,337 A * | 12/1999 | Blosser | F02D 41/0055 60/274 |
| 6,426,226 B1 * | 7/2002 | Senkan | B01J 19/0046 250/281 |
| 6,865,472 B2 | 3/2005 | Nakamura | |
| 7,968,055 B2 | 6/2011 | Brothier et al. | |
| 9,689,864 B2 * | 6/2017 | Ahmad | G01N 33/52 |
| 2003/0089854 A1 | 5/2003 | Shifflett et al. | |
| 2004/0069948 A1 * | 4/2004 | Feisst | G02B 6/1225 250/343 |
| 2004/0138499 A1 * | 7/2004 | Buschulte | C07C 51/252 562/545 |
| 2007/0089404 A1 * | 4/2007 | Gross | F01N 3/2066 60/286 |
| 2009/0028209 A1 * | 1/2009 | Feitisch | G01N 21/39 374/35 |
| 2009/0229250 A1 * | 9/2009 | Yamakage | G01N 21/3504 60/276 |
| 2010/0264315 A1 | 10/2010 | Okada et al. | |
| 2013/0045541 A1 * | 2/2013 | Fix | G01N 21/3504 436/164 |
| 2015/0330281 A1 * | 11/2015 | Ashitaka | F01P 7/04 123/41.12 |
| 2016/0041359 A1 * | 2/2016 | Gaskin | G01N 21/39 250/573 |
| 2016/0289090 A1 * | 10/2016 | Liao | C02F 1/008 |
| 2016/0305870 A1 | 10/2016 | Ooyama et al. | |
| 2016/0320361 A1 * | 11/2016 | Johansen | G01N 33/0013 |
| 2018/0088037 A1 * | 3/2018 | Liu | G01N 21/01 |
| 2018/0223756 A1 | 8/2018 | Benson et al. | |
| 2018/0321138 A1 * | 11/2018 | Li | G01N 21/8507 |
| 2019/0203623 A1 * | 7/2019 | Yoo | F01N 3/2066 |
| 2019/0277819 A1 * | 9/2019 | Solomon | B01D 46/0063 |

* cited by examiner

OPTICAL SENSOR FOR AFTERTREATMENT CATALYST CONDITION

TECHNICAL FIELD

The present disclosure generally relates to aftertreatment systems for engines and, more specifically, to sensors for aftertreatment systems that optically detect a condition of an aftertreatment catalyst and to control engine operation based on the detected condition of the aftertreatment catalyst.

BACKGROUND

Aftertreatment systems are used to treat the exhaust emitted by an internal combustion engine prior to the release of the exhaust to the environment. An aftertreatment system reduces the emission of harmful pollutants such as carbon monoxide, hydrocarbons, and nitrogen oxides ($NO_x$) to innocuous products such as carbon dioxide, water, and nitrogen. An aftertreatment system may include a series of aftertreatment units having an aftertreatment catalyst that each catalytically convert certain pollutants in the exhaust stream. For example, a diesel oxidation catalyst (DOC) catalyzes the oxidation of carbon monoxide and hydrocarbons in the exhaust stream into carbon dioxide and water. A selective catalytic reduction (SCR) catalyst may catalyze the reduction of $NO_x$ in the exhaust stream to nitrogen and water. Each of the aftertreatment catalysts in the aftertreatment system may include a catalyst brick having a honeycomb structure onto which the active metal catalysts are coated or deposited.

Aftertreatment catalysts may experience a change in condition during the various stages of operation of the engine. For instance, an aftertreatment catalyst may change color during operation due to changes in the oxidation states of the metal catalysts. Additionally, under idle conditions when the exhaust gas and the aftertreatment catalysts are at lower temperatures, unburned hydrocarbons may be absorbed into the pores of the catalyst brick due to the lower vapor pressure of the hydrocarbons. As the aftertreatment catalyst temperature increases when the engine shifts to normal operation conditions, the absorbed hydrocarbons may be released from the catalyst by evaporation or oxidized to regenerate the catalyst. However, if the hydrocarbon loading on the aftertreatment catalyst reaches a critical level and the aftertreatment catalyst temperature rises above a certain temperature, the rate of removal and oxidation of the hydrocarbons may cause high amounts of local heat to be generated on the aftertreatment catalyst that could damage the catalytic material. Monitoring the hydrocarbon loading or other conditions of the aftertreatment catalyst may indicate how to safely operate the engine, or provide information as to the operation state of the engine or the efficiency of the catalyst.

US Patent Application Publication Number 2018/0223756 describes an aftertreatment system including an aftertreatment component having an inlet to receive untreated exhaust gas, an outlet to release the treated exhaust gas, and a DOC, a SCR catalyst, and a diesel particulate filter (DPF) between the inlet and the outlet. The aftertreatment system described by the publication includes a monitoring arrangement that estimates a mass of hydrocarbons absorbed or retained by the aftertreatment component using sensors placed at the inlet and the outlet of the aftertreatment component. The amount of absorbed hydrocarbons is derived based on the temperature or pressure differential between the inlet and the outlet detected by the sensors, the density and viscosity of the exhaust gas detected by the sensors, changes in conductivity of the sensors, or other values detected by the sensors. While effective, there is still a need for improved or alternative strategies for sensing the hydrocarbon loading of an aftertreatment catalyst, as well as other condition changes to the aftertreatment catalyst.

SUMMARY

In accordance with one aspect of the present disclosure, an aftertreatment system for an engine system is disclosed. The aftertreatment system may comprise an aftertreatment catalyst and an optical sensor mounted on the aftertreatment catalyst. The optical sensor may include a light source configured to illuminate the aftertreatment catalyst with light, and an optical detector configured to measure an amount of the light absorbed by the aftertreatment catalyst upon illumination with the light. The measured amount of the light absorbed by the aftertreatment catalyst may correlate with a condition parameter of the aftertreatment catalyst.

In accordance with another aspect of the present disclosure, an optical sensor for an aftertreatment catalyst of an aftertreatment system for an engine system is disclosed. The optical sensor may be configured to mount to the aftertreatment catalyst when the engine system is not in operation. The optical sensor may comprise a light source configured to illuminate the aftertreatment catalyst with light when mounted to the aftertreatment catalyst, and an optical detector configured to measure an amount of the light absorbed by the aftertreatment catalyst when illuminated with the light. The optical sensor may further comprise an electronic device configured to determine a condition parameter of the aftertreatment catalyst based on the measured amount of the light absorbed by the aftertreatment catalyst, and to display the condition parameter at a display.

In accordance with another aspect of the present disclosure, a method for determining a condition parameter of an aftertreatment catalyst of an aftertreatment system for an engine system is disclosed. The method may comprise illuminating the aftertreatment catalyst with light from a light source mounted on the aftertreatment catalyst, and detecting an amount of the light absorbed by the aftertreatment catalyst with an optical detector mounted on the aftertreatment catalyst. The method may further comprise determining the condition parameter of the aftertreatment catalyst based on the detected amount of the light absorbed by the aftertreatment catalyst.

These and other aspects and features of the present disclosure will be more readily understood when read in conjunction with the accompanying drawings.

DETAILED DESCRIPTION

Figure 1:
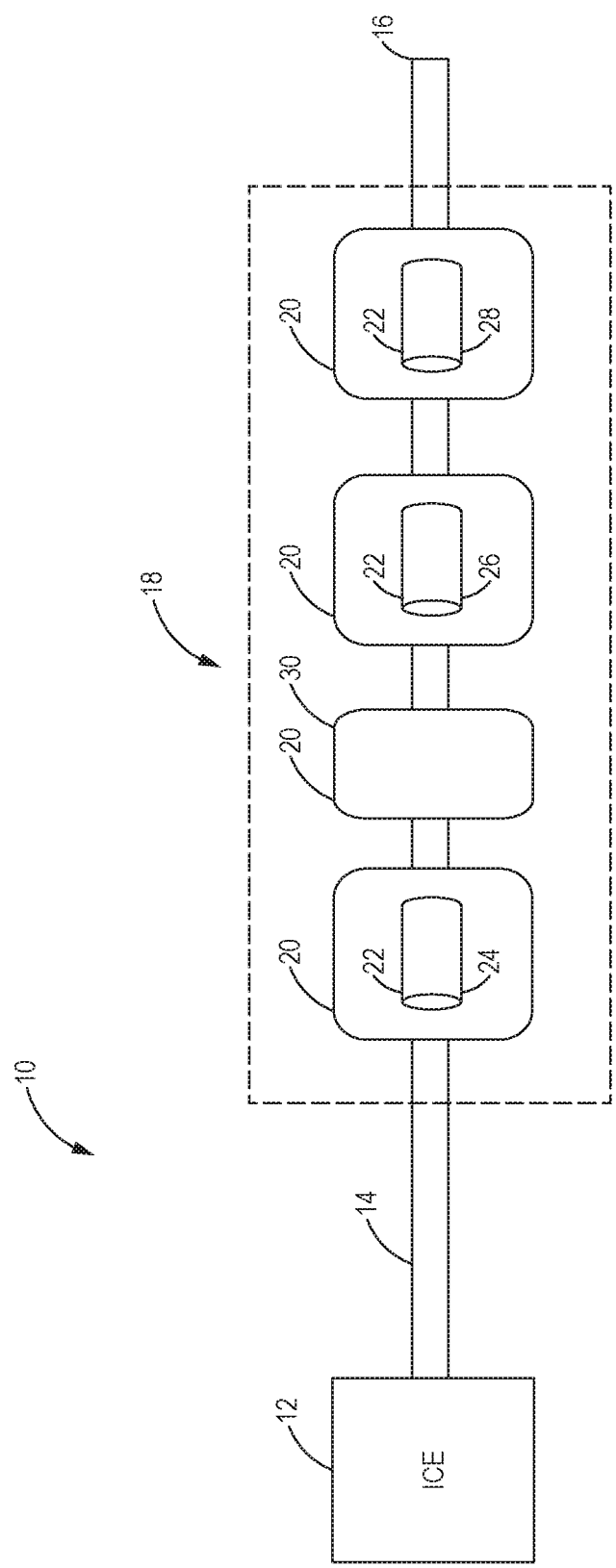
FIG. 1 is a schematic representation of an engine system having an aftertreatment system with aftertreatment catalysts, in accordance with the present disclosure.

Referring now to the drawings, and with specific reference to FIG. 1, an engine system 10 is shown. The engine system 10 may include an internal combustion engine 12 that combusts a fuel to generate an exhaust, and an exhaust conduit 14 carries the exhaust to a tail pipe 16 for release of the exhaust to the atmosphere. An aftertreatment system 18 disposed in the exhaust conduit 14 may treat the exhaust gas prior to release to the atmosphere. The engine 12 may be a diesel engine that burns diesel fuel, or a mixed fuel engine that burns both diesel fuel and one or more other fuels such as natural gas. The engine 12 may provide mechanical energy used in various construction, agricultural, industrial, commercial, transportation, or marine applications. For example, the engine system 10 may be used to provide mechanical energy to drive machines such as off-highway trucks, mining equipment, tractors, excavators, dozers, and wheel loaders.

The aftertreatment system 18 may include a plurality of aftertreatment units 20 each designed to remove or catalytically convert specific environmental pollutants in the exhaust stream. Some of the aftertreatment units 20 may have an aftertreatment catalyst 22 that catalyzes the conversion of the pollutants. The aftertreatment catalyst 22 may include a cylindrical catalyst brick having a porous honeycomb structure, and an active catalytic material such as a metal catalyst coated or deposited in the pores of the catalyst brick. One of the aftertreatment units 20 may include a diesel oxidation catalyst (DOC) 24 as the aftertreatment catalyst 22 that catalyzes the conversion of carbon monoxide and hydrocarbons in the exhaust stream to carbon dioxide and water. In addition, another of the aftertreatment units 20 may include a selective catalytic reduction (SCR) catalyst 26 as the aftertreatment catalyst 22 that catalyzes the reduction of nitrogen oxides (No) in the exhaust stream to nitrogen and water. Furthermore, another of the aftertreatment units 20 may include an ammonia oxidation catalyst 28 as the aftertreatment catalyst 22. One of the aftertreatment units 20 may be a diesel particulate filter (DPF) 30 that filters particulate matter or soot from the exhaust stream. It will be understood that the order and number of aftertreatment units 20 shown in FIG. 1 is merely exemplary and may vary in practice. For example, the DPF 30 may be upstream or downstream from the SCR catalyst 26. Furthermore, other types of aftertreatment units apparent to those with ordinary skill in the art may also be included in the aftertreatment system 18.

Figure 2:
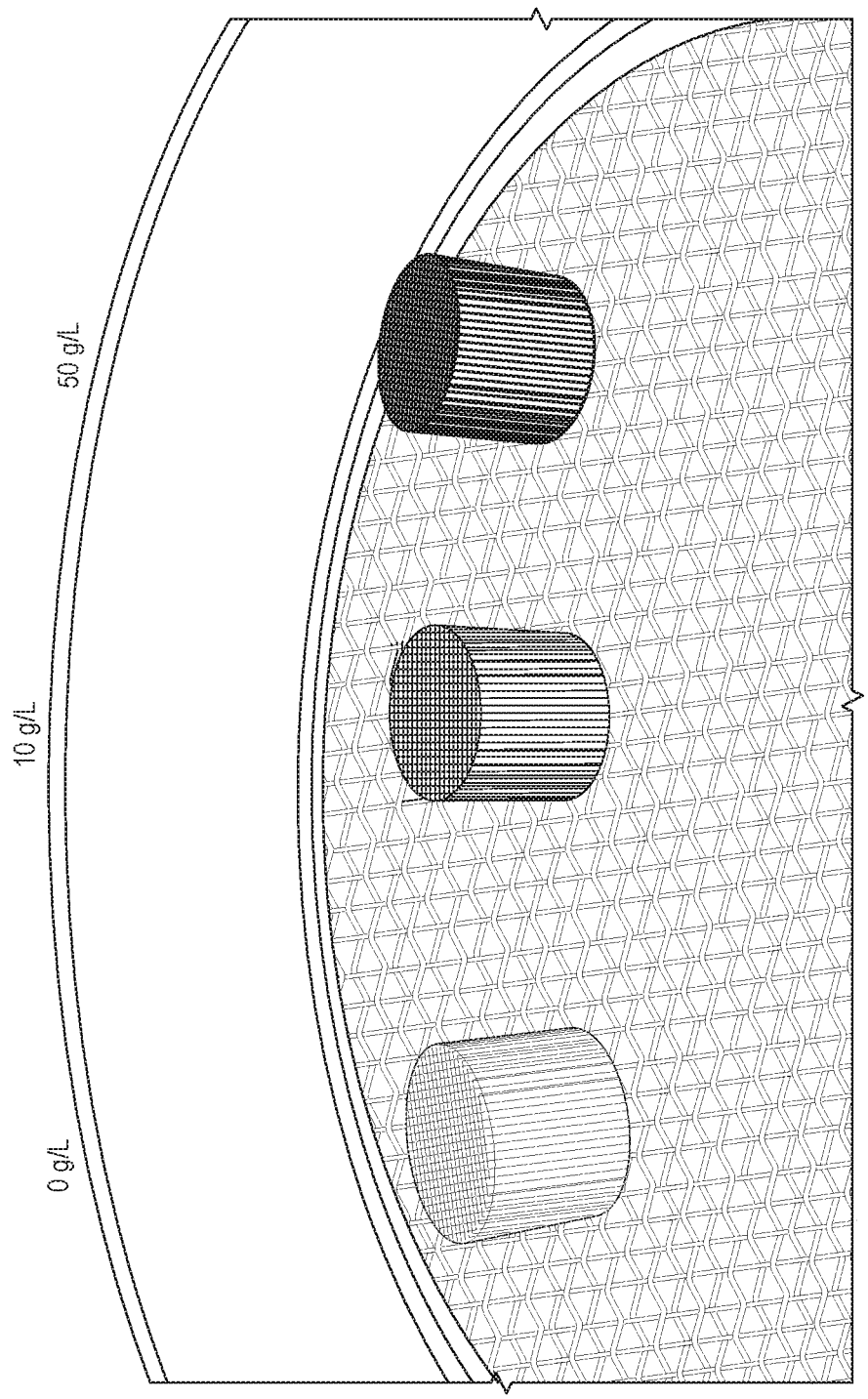
FIG. 2 is a photograph of color changes in a selective catalytic reduction (SCR) catalyst with increasing hydrocarbon loading, in accordance with the present disclosure.

During the operation of the engine system 10, the condition of the aftertreatment catalysts 22 may change and may be reflected by a visible color change at the catalyst 22. For example, the active metal catalysts may change oxidation state causing the color of the aftertreatment catalyst 22 to change. In addition, Applicant has observed that the aftertreatment catalysts 22 (including the diesel oxidation catalyst 24, the SCR catalyst 26, and the ammonia oxidation catalyst 28) become darker in color with increasing hydrocarbon loading on the aftertreatment catalyst. FIG. 2 shows the darkening color of an SCR catalyst as the hydrocarbon loading on the catalyst increases from 0 g/L (left), to 10 g/L (middle), to 50 g/L (right). As such, visible changes in the color of the aftertreatment catalyst 22 may be used to detect specific condition parameters of the aftertreatment catalyst 22 (e.g., hydrocarbon loading, oxidation state, etc.).

Figure 3:
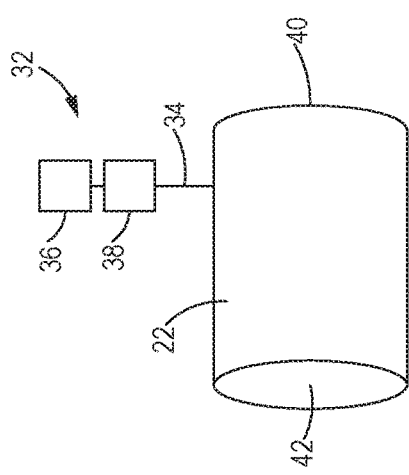
FIG. 3 is a side view of an aftertreatment catalyst of the aftertreatment system having an optical sensor for detecting a condition parameter of the aftertreatment catalyst, constructed in accordance with the present disclosure.

Turning now to FIG. 3, an optical sensor 32 for sensing a condition parameter of one or more of the aftertreatment catalysts 22 of the aftertreatment system 18 is shown. For example, the optical sensor 32 may be mounted to the catalyst brick of one or more of the DOC 24, the SCR catalyst 26, the ammonia oxidation catalyst 28, or other aftertreatment catalysts 22 in the aftertreatment system 18. The optical sensor 32 may include a probe 34 that mounts to the catalyst 22 and carries a light source 36 and an optical detector 38. The light source 36 may illuminate the aftertreatment catalyst 22 with light, and the optical detector 38 may measure the amount of light that is absorbed by the aftertreatment catalyst 22 upon illumination with the light source 36. As explained further below, the measured amount of light absorbed by the aftertreatment catalyst 22 may be correlated with a condition parameter (e.g., hydrocarbon loading, oxidation state, etc.) of the aftertreatment catalyst 22, and the condition parameter may be used as a basis to control the operation of the engine 12. As used herein, the condition parameter of the aftertreatment catalyst 22 is any measurable condition of the aftertreatment catalyst 22 that can be derived from a color change of the catalyst 22.

Figure 4:
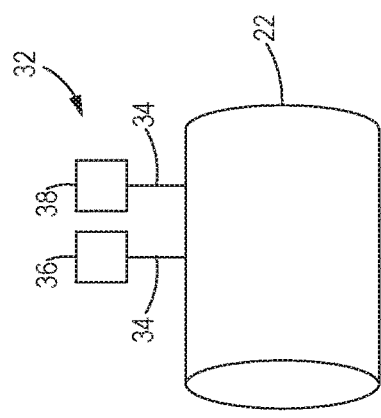
FIG. 4 is a side view similar to FIG. 3, but with the optical sensor having a light source and an optical detector mounted separately on the aftertreatment catalyst, constructed in accordance with the present disclosure.
Figure 6:
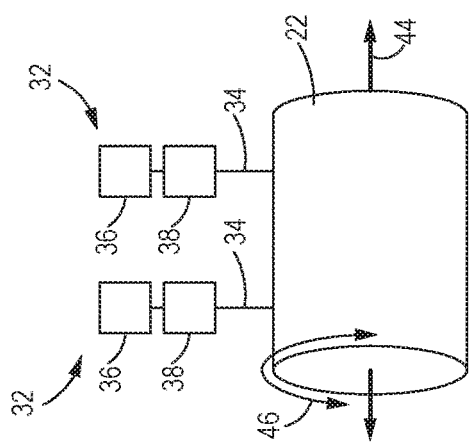
FIG. 6 is a side view similar to FIG. 3, but having two optical sensors mounted at different positions along the aftertreatment catalyst, constructed in accordance with the present disclosure.
Figure 5:
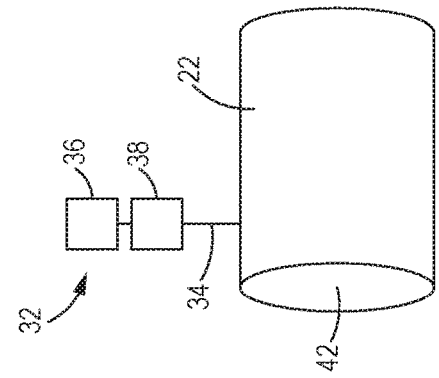
FIG. 5 is a side view similar to FIG. 3, but with the optical sensor mounted near an inlet face of the aftertreatment catalyst, constructed in accordance with the present disclosure.

As shown in FIG. 3, the optical sensor 32 may be mounted near or at an outlet face 40 of the aftertreatment catalyst 22. Mounting the optical sensor 32 at or near the outlet face 40 may be beneficial, for example, if the DPF 30 is downstream of the aftertreatment catalyst 22 such that particulate matter or soot at an inlet face 42 of the catalyst 22 could interfere with the accuracy of the measurements. The light source 36 and the optical detector 38 may be mounted together on the probe 34 as shown in FIG. 3, or the light source 36 and the optical detector 38 may be mounted separately on the aftertreatment catalyst 22 on separate probes 34 as shown in FIG. 4. Alternatively, the optical sensor 32 may be mounted at or near the inlet face 42 of the aftertreatment catalyst 22 (see FIG. 5), such as when the DPF 30 is upstream of the aftertreatment catalyst 22. As yet another alternative arrangement, the aftertreatment catalyst 22 may have two or more optical sensors 32 each having a light source 36 and an optical detector 38 mounted on separate probes 34 (see FIG. 6). In the latter arrangement, the optical sensors 32 may be axially spaced from each other with respect to a longitudinal axis 44 of the aftertreatment catalyst 22, and radially spaced from each other with respect to a circumferential axis 46 of the aftertreatment catalyst 22. Radial and axial spacing of the optical sensors 32 may prevent the measurements made by the optical sensors 32 from interfering with each other. Other possible arrangements may include combinations of the configurations shown in FIGS. 3-6. For example, the light source 36 and the optical detector 38 may be mounted on separate probes 34 near or at the inlet face 42 of the catalyst 22.

The light emitted by the light source 36 may be visible light with wavelengths across the visible spectrum, and the optical detector 38 may measure the visible light absorbance by the aftertreatment catalyst 22 at wavelengths across the visible spectrum. Alternatively, the light emitted by the light source 36 may be visible light in a narrow range or at a specific wavelength within the visible spectrum, and the optical detector 38 may be configured to measure the amount of light absorbed by the aftertreatment catalyst 22 in the narrow range of wavelengths or at the specific wavelength within the visible spectrum.

Figure 7:
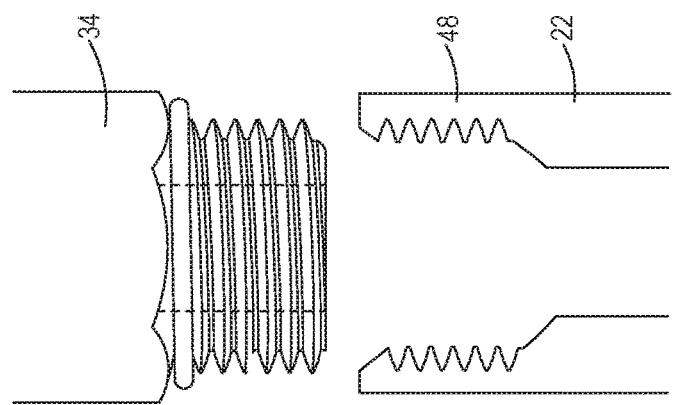
FIG. 7 is a side view illustrating a mechanical connection between the optical sensor and the aftertreatment catalyst, constructed in accordance with the present disclosure.

Turning now to FIG. 7, an exemplary mechanical connection between the probe 34 and the aftertreatment catalyst 22 is shown. In this example, a boss 48 may be attached within the porous body of the catalyst brick, and the probe 34 may be attached and mounted to the catalyst 22 by a threaded connection to the boss 48. However, other suitable mechanical or chemical methods for attaching or mounting the optical sensor 32 to the aftertreatment catalyst 22 may also be used.

Figure 8:
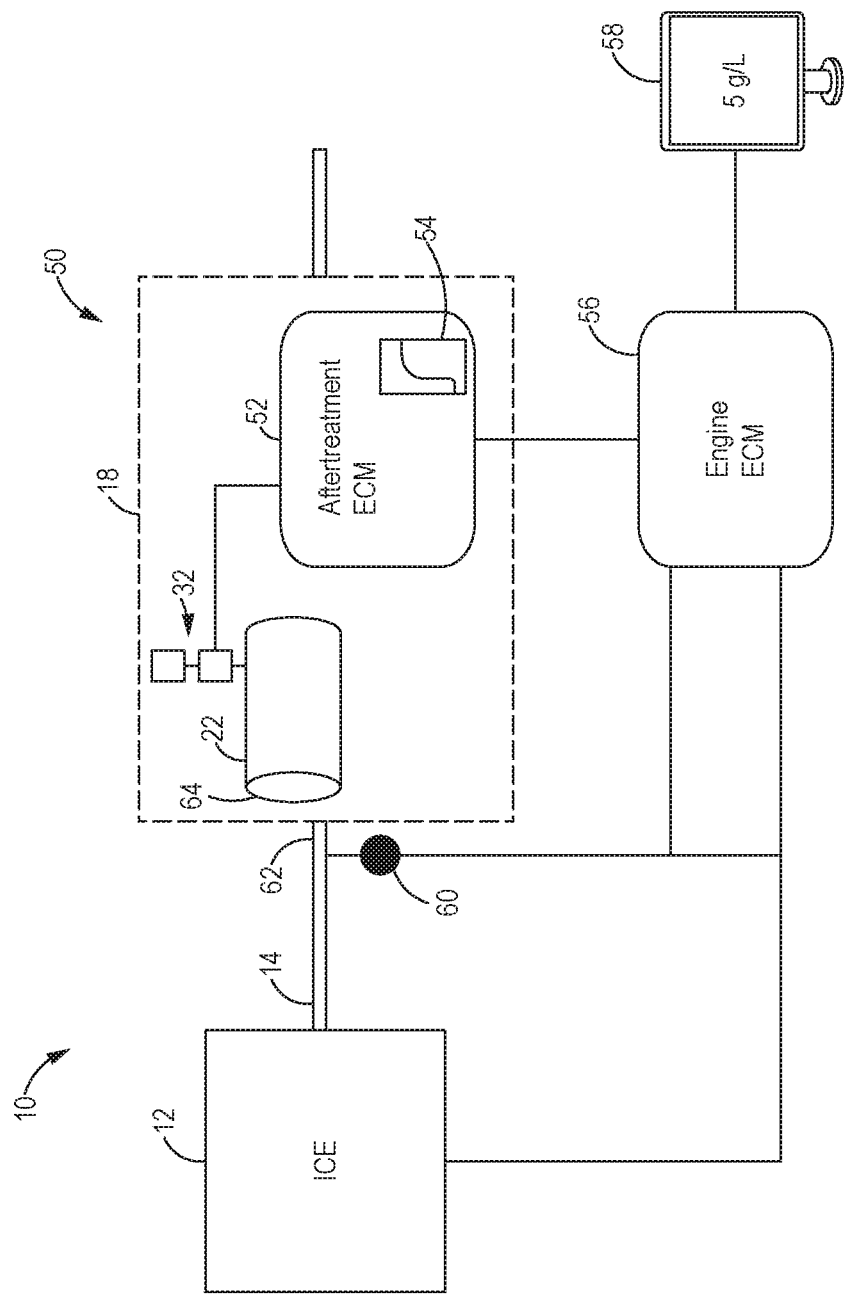
FIG. 8 is a schematic representation of a control system for controlling engine operation based on the condition parameter of the aftertreatment catalyst detected by the optical sensor, in accordance with the present disclosure.

FIG. 8 shows a control system 50 that determines the condition parameter of the aftertreatment catalyst 22 based on the measurements made by the optical sensor 32, and controls the engine 12 according to the determined condition parameter. It is noted that FIG. 8 only shows one aftertreatment catalyst 22 in the aftertreatment system 18 for simplicity purposes. The control system 50 may include an aftertreatment electronic control module (ECM) 52 associated with the aftertreatment system 18 and in electronic communication with the optical sensor 32. The optical sensor 32 may transmit signals indicative of the measured amount of light absorbed by the aftertreatment catalyst 22 to the aftertreatment ECM 52, and the aftertreatment ECM 52 may determine the condition parameter of the aftertreatment catalyst 22 based on the signals received from the optical sensor 32. For example, to determine the hydrocarbon loading of the aftertreatment catalyst 22, the aftertreatment ECM 52 may compare the received absorbance signals with one or more calibration maps 54 stored in a memory of the ECM 52 that relate known hydrocarbon loading values to catalyst light absorbance values at the specific mounting position of the optical sensor 32 along the aftertreatment catalyst 22. The calibration maps 54 may include an offset calibration map that allows the determination of the total hydrocarbon loading over the entire aftertreatment catalyst 22. For example, if the optical sensor 32 is mounted near the outlet face 40 where hydrocarbon loading is lower compared to the inlet face 42, the offset calibration map may allow the hydrocarbon loading over the entire aftertreatment catalyst 22 to be extrapolated from the measurements made near the outlet face 40.

The control system 50 may further include an engine electronic control module (ECM) 56 that controls and monitors various functions of the engine system 10. The engine ECM 56 may be in communication with the aftertreatment ECM 52 and may receive signals from the aftertreatment ECM 52 indicating the condition parameter (e.g., hydrocarbon loading, oxidation state, etc.) of the aftertreatment catalyst 22. In response to the received signals, the engine ECM 56 may transmit the measured condition parameter for viewing at a display 58, such as a computer monitor or a handheld device display, to notify an operator of the current condition of the aftertreatment catalyst 22. For instance, if the measured condition parameter is the hydrocarbon loading, the engine ECM 56 may transmit the hydrocarbon loading and continually update the current hydrocarbon loading at the display 58. In addition, the engine ECM 56 may also determine if the condition parameter is above a predetermined threshold and transmit a warning signal for viewing at the display 58 if the condition parameter is above the predetermined threshold. For example, if the hydrocarbon loading of the aftertreatment catalyst 22 is above the predetermined threshold, the warning signal at the display 58 may notify the operator to reduce or minimize the speed and/or the load on the engine 12 to prevent the exhaust and the aftertreatment catalyst 22 from reaching temperatures that could damage the catalyst 22 due to high rates of hydrocarbon removal from the catalyst 22.

In some arrangements, the engine ECM 56 may control or alter the operation of the engine 12 autonomously or in conjunction with the operator based on the measured condition parameter of the aftertreatment catalyst 22. For example, if the hydrocarbon loading of the aftertreatment catalyst 22 is above the predetermined threshold, the engine ECM 56 may transmit commands to derate the engine 12 by reducing the engine speed and/or the engine load to keep the temperature of the aftertreatment catalyst 22 below a predetermined temperature threshold above which the aftertreatment catalyst 22 could be damaged. In this regard, the engine ECM 56 may be in communication with the engine 12, as well as a temperature sensor 60 that monitors the temperature of the exhaust at an inlet 62 of the aftertreatment system 18 or at an inlet 64 of the aftertreatment catalyst 22. The exhaust temperature at the inlets 62 and 64 may match or closely match the temperature of the aftertreatment catalyst 22. The engine ECM 56 may continue to transmit commands to control the engine operation by speed and/or load limitations until the hydrocarbon loading falls below the predetermined threshold.

In alternative arrangements, the functions of the aftertreatment ECM 52 and the engine ECM 56 described herein may vary or may be performed by a single ECM or more than two ECMs in communication with each other. For example, the aftertreatment ECM 52 rather than the engine ECM 56 may transmit the condition parameter and warning signals for viewing at the display 58. As another example, a single ECM, such as the engine ECM 56, may be configured to receive signals from the optical sensor 32, determine the catalyst condition parameter from the received signals, transmit the condition parameter and warning signals to the display 58, and control the engine operation based on the catalyst condition parameter.

Figure 9:
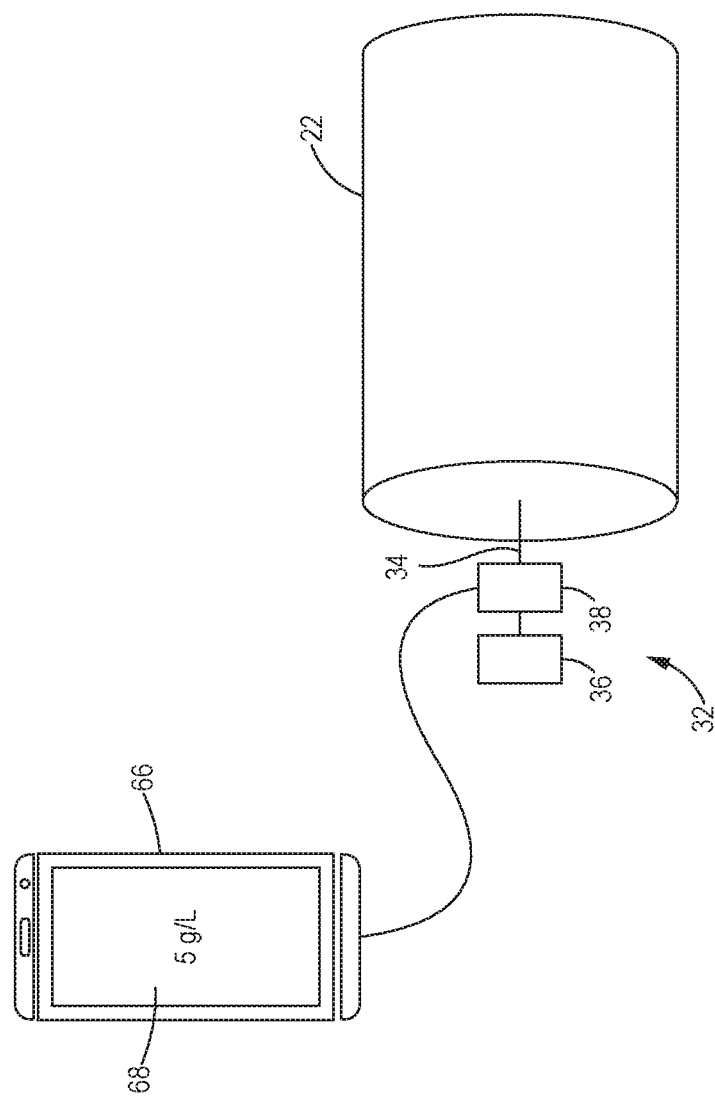
FIG. 9 is a schematic representation of applying the optical sensor as a service tool for detecting the condition parameter of the aftertreatment catalyst when the engine is off, constructed in accordance with the present disclosure.

In an alternative arrangement depicted in FIG. 9, the optical sensor 32 may be used as a service tool to monitor the condition parameter of the aftertreatment catalyst 22 when the engine system 10 is not in operation. In this arrangement, the probe 34 of the optical sensor 32 may be connected to an accessible face (e.g., the inlet face 42, the outlet face 40, a side face) of the aftertreatment catalyst 22 when the engine system 10 is shut down, and measurements of the visible light absorbance of the catalyst 22 may be taken using the light source 36 and the optical detector 38 as described above. To attach the probe 34 to the aftertreatment catalyst 22, a cap may be removed from the boss 48 and the probe 34 may be connected to the boss 48 by the threaded connection as described above (see FIG. 7). However, other suitable mechanical or chemical attachment arrangements may also be used. As described above in relation to FIGS. 3-6, the light source 36 and the optical detector 38 may be mounted together on the catalyst 22 on the same probe 34, or separately from each other on different probes 34.

As shown in FIG. 9, the optical sensor 32 may be in electronic (or wireless) communication with an electronic device 66, and may transmit signals indicative of the light absorbance of the catalyst 22 to the electronic device 66. The electronic device 66 may be configured to determine the condition parameter of the catalyst 22 based on the received signals and display the condition parameter at a display 68. For example, the electronic device 66 may determine the hydrocarbon loading on the catalyst 22 using one or more calibration maps stored in a memory of the device 66 that relate known hydrocarbon loading values to catalyst absorbance values. The calibration maps may include an offset calibration map as described above to allow the total hydrocarbon loading over the entire aftertreatment catalyst 22 to be derived from measurements at one position along the catalyst 22. The electronic device 66 may be a handheld device, such as a smartphone, tablet, laptop, or other handheld computer with a display, or it may be a stationary computer with a display.

INDUSTRIAL APPLICABILITY

In general, the teachings of the present disclosure may find applicability in many industries including, but not limited to, construction, agricultural, mining, industrial, commercial, transportation, or marine applications. More specifically, the teachings of the present disclosure may find applicability in any industry relying on engine systems having aftertreatment catalysts for treating the engine exhaust.

Figure 10:
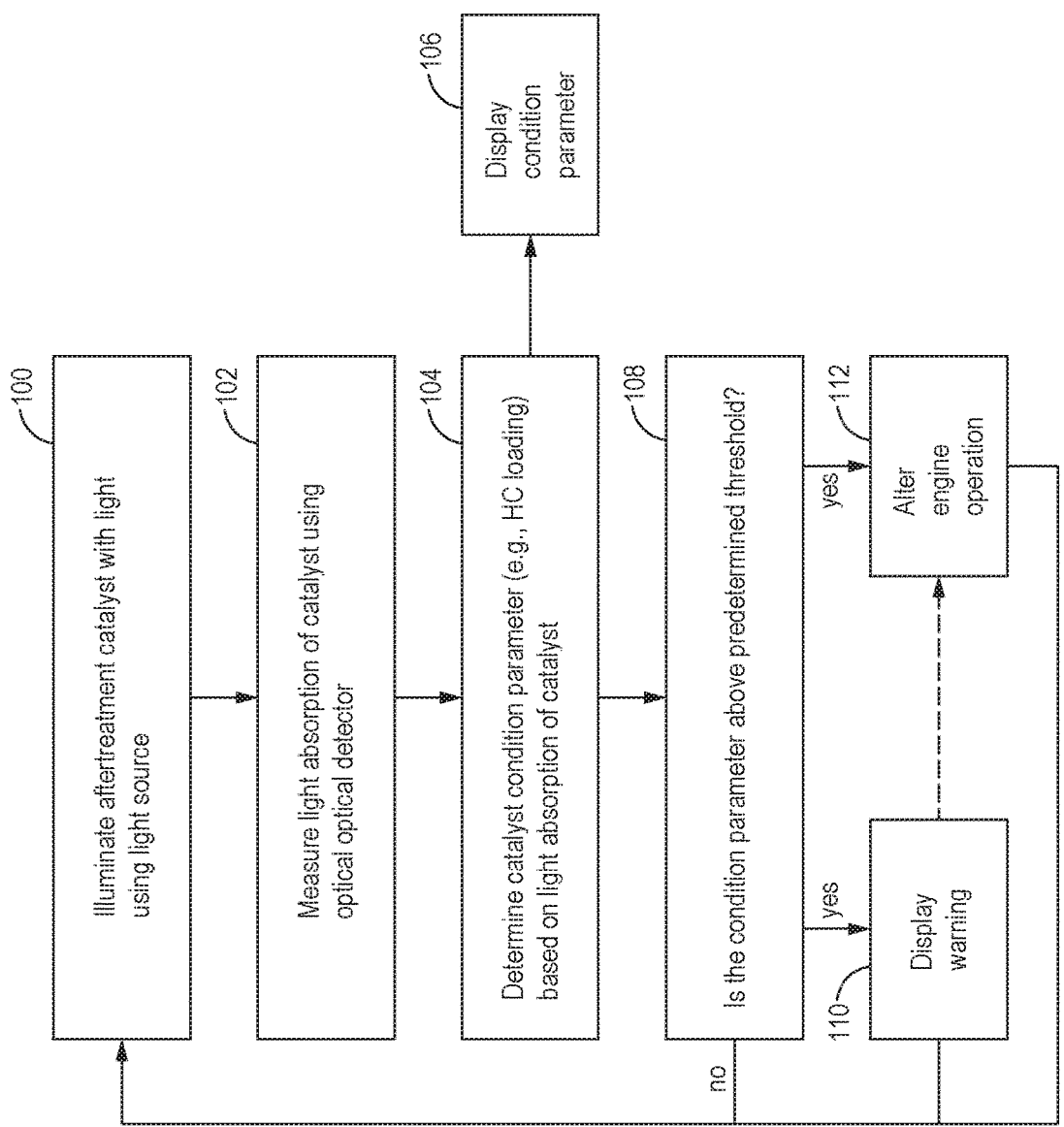
FIG. 10 is a flowchart of a series of steps that may be involved in detecting the condition parameter of the aftertreatment catalyst with the optical sensor, and in controlling the engine operation according to the condition parameter of the aftertreatment catalyst, in accordance a method of the present disclosure.

FIG. 10 shows a series of steps that may be involved in sensing a condition parameter (e.g., hydrocarbon loading, oxidation state, etc.) of the aftertreatment catalyst 22 using the optical sensor 32, and in controlling the engine operation according to the condition parameter of the aftertreatment catalyst 22. At a first block 100, light may be emitted from the light source 36 on the aftertreatment catalyst 22 to illuminate the aftertreatment catalyst 22. At a next block 102, the optical detector 38 may measure the absorbance of the light by the aftertreatment catalyst 22. The condition parameter of the aftertreatment catalyst 22 may be determined from the measured light absorbance of the catalyst 22 (block 104), and the condition parameter of the catalyst 22 may be displayed at the display 58 or the display 68 (block 106). For example, the blocks 104 and 106 may be performed by the aftertreatment ECM 52 and the engine ECM 56, or by the electronic device 66 (e.g., handheld device) if the optical sensor 32 is used as a service tool when the engine system 10 is not in operation.

At a next block 108, the engine ECM 56 (or the aftertreatment ECM 52) or the electronic device 66 may determine if the condition parameter is above a predetermined threshold. If the condition parameter is below the threshold, the condition parameter may be continued to be monitored by repeating the blocks 100, 102, 104, 106, and 108. If the condition parameter is above the predetermined threshold, a warning signal may be displayed at the display 58 or the display 68 to notify the operator (block 110). The block 110 may be performed by the engine ECM 56 or the aftertreatment ECM 52, or by the electronic device 66 when the optical sensor 32 is employed as a service tool. The warning signal may notify the operator to alter the operation of the engine 12 (block 112), such as by reducing the engine speed and/or reducing the load on the engine until the condition parameter falls below the threshold and the warning signal disappears. Alternatively or in addition to this, changes in the engine operation (block 112) may be controlled by the engine ECM 56 as described above. The block 112 may be continued until the condition parameter falls below the predetermined threshold.

The optical sensor disclosed herein allows a condition of an aftertreatment catalyst to be determined based on color changes that occur at the aftertreatment catalyst. The optical sensor may be mounted directly on the aftertreatment catalyst, and may include a light source to illuminate the catalyst and an optical detector to measure the amount of the light absorbed by the catalyst. A catalyst condition parameter may be determined based on the measured amount of light absorbed by the catalyst, and the operation of the engine may be altered or limited accordingly. For example, the condition parameter may be hydrocarbon loading on the aftertreatment catalyst, and the engine may be derated by limiting the engine speed and/or load on the engine when the hydrocarbon loading of the catalyst is above a threshold value. Deration of the engine may prevent the temperature of the aftertreatment catalyst from reaching temperatures at which damage to the aftertreatment catalyst could occur due to high rates of hydrocarbon removal from the catalyst (via evaporation or oxidation). Alterations in the engine operation may be controlled by the operator and/or electronically by the engine ECM. In one implementation, the optical sensor may be employed as a service tool wherein the condition of the aftertreatment catalyst is determined when the engine is shut down. The optical sensor disclosed herein provides a direct and accurate approach to determine a condition of the aftertreatment catalyst based on the color changes of the aftertreatment catalyst that occur as the condition of the aftertreatment catalyst changes.

What is claimed is:

1. An aftertreatment system for an engine system, the aftertreatment system comprising:
    an aftertreatment catalyst including a catalyst brick containing an active catalytic material; and
    an optical sensor mounted on the aftertreatment catalyst, the optical sensor including
        a light source aimed at the active catalytic material along a direct optical path between the light source and the active catalytic material, such that a light from the light source illuminates the catalyst brick through incidence of the light onto the catalyst brick, and
        an optical detector aimed at the active catalytic material along a direct optical path between the optical detector and the active catalytic material, the optical detector being configured to measure an amount of the light absorbed by the catalyst brick upon illumination with the light, the measured amount of the light absorbed by the catalyst brick correlating with a condition parameter of the catalyst brick.

2. The aftertreatment system of claim 1, further comprising an electronic control module (ECM) in electronic communication with the optical sensor, wherein the optical sensor transmits signals indicative of the measured amount of the light absorbed by the catalyst brick to the ECM.

3. The aftertreatment system of claim 2, wherein the ECM is configured to determine the condition parameter based on the signals indicative of the measured amount of the light absorbed by the catalyst brick.

4. The aftertreatment system of claim 3, wherein the ECM is further configured to alter an operation of an engine of the engine system in response to the condition parameter being above a predetermined threshold.

5. The aftertreatment system of claim 4, wherein the optical sensor is mounted at an outlet face of the aftertreatment catalyst.

6. The aftertreatment system of claim 4, wherein the optical sensor is mounted at an inlet face of the aftertreatment catalyst.

7. The aftertreatment system of claim 4, wherein the light source and the optical detector are mounted separately on the aftertreatment catalyst.

8. The aftertreatment system of claim 4, wherein the aftertreatment catalyst is one of a selective catalytic reduction (SCR) catalyst and a diesel oxidation catalyst (DOC).

9. The aftertreatment system of claim 4, wherein the light is visible light.

10. The aftertreatment system of claim 4, wherein the light is visible light at a specific wavelength, and wherein the optical detector is configured to measure the amount of the visible light absorbed by the catalyst brick at the specific wavelength.

11. The aftertreatment system of claim 4, wherein the condition parameter is a hydrocarbon loading on the catalyst brick.

12. The aftertreatment system of claim 11, wherein the ECM is configured to transmit commands to the engine to derate the engine in response to the hydrocarbon loading being above the predetermined threshold to keep a temperature of the aftertreatment catalyst below a temperature threshold.

13. A method for determining a condition parameter of an aftertreatment catalyst of an aftertreatment system for an engine system, the aftertreatment catalyst including a catalyst brick containing an active catalytic material, the method comprising:
  illuminating a catalyst brick of the aftertreatment catalyst with light from a light source mounted on the aftertreatment catalyst and aimed at the active catalytic material;
  detecting an amount of the light absorbed by the catalyst brick with an optical detector mounted on the aftertreatment catalyst and aimed at the active catalytic material; and
  determining the condition parameter of the aftertreatment catalyst based on the detected amount of the light absorbed by the catalyst brick.

14. The method of claim 13, wherein determining the condition parameter of the aftertreatment catalyst is performed by an electronic control module (ECM) of the engine system.

15. The method of claim 14, further comprising using the ECM to alter an operation of an engine of the engine system in response to the condition parameter being above a predetermined threshold.

16. The method of claim 15, wherein the condition parameter is a hydrocarbon loading on the aftertreatment catalyst.

17. The method of claim 16, wherein using the ECM to alter the operation of the engine comprises derating the engine in response to the hydrocarbon loading being above the predetermined threshold to keep a temperature of the aftertreatment catalyst below a temperature threshold.

* * * * *